US010433752B2

(12) United States Patent
Faul et al.

(10) Patent No.: US 10,433,752 B2
(45) Date of Patent: Oct. 8, 2019

(54) METHOD FOR THE REAL-TIME IDENTIFICATION OF SEIZURES IN AN ELECTROENCEPHALOGRAM (EEG) SIGNAL

(75) Inventors: Stephen Daniel Faul, County Cork (IE); Andriy Temko, County Cork (IE); William Peter Marnane, County Cork (IE); Gordon Lightbody, County Cork (IE); Geraldine Bernadette Boylan, County Cork (IE)

(73) Assignee: National University of Ireland, County Cork (IE)

( * ) Notice: Subject to any disclaimer, the term of this patent is extended or adjusted under 35 U.S.C. 154(b) by 237 days.

(21) Appl. No.: 13/262,891

(22) PCT Filed: Apr. 7, 2010

(86) PCT No.: PCT/EP2010/054612
§ 371 (c)(1),
(2), (4) Date: Dec. 22, 2011

(87) PCT Pub. No.: WO2010/115939
PCT Pub. Date: Oct. 14, 2010

(65) Prior Publication Data
US 2012/0101401 A1 Apr. 26, 2012

(30) Foreign Application Priority Data

Apr. 7, 2009 (GB) .................................. 0906029.4

(51) Int. Cl.
A61B 5/04 (2006.01)
A61B 5/00 (2006.01)
(Continued)

(52) U.S. Cl.
CPC .......... *A61B 5/0476* (2013.01); *A61B 5/4094* (2013.01); *A61B 5/7267* (2013.01); *G06K 9/00536* (2013.01)

(58) Field of Classification Search
CPC . A61B 5/0476; A61B 5/04012; A61B 5/4094; A61B 5/7264; A61B 5/7267
(Continued)

(56) References Cited

U.S. PATENT DOCUMENTS 4,913,160 A * 4/1990 John .............................. 600/544
5,467,777 A * 11/1995 Farwell ......................... 600/544
(Continued)

FOREIGN PATENT DOCUMENTS

WO   WO 2009005734 A2 * 1/2009

OTHER PUBLICATIONS

Chaovalitwongse et al. On the Time Series Support Vector Machine Using Dynamic Time Warping Kernel for Brain Activity Classification. Cybernetics and Systems Analysis, vol. 44, No. 1, 2008.*
(Continued)

*Primary Examiner* — Etsub D Berhanu
(74) *Attorney, Agent, or Firm* — Valauskas Corder LLC

(57) ABSTRACT

The present invention relates to a method for the real-time identification of seizures in an Electroencephalogram (EEG) signal. The method provides for patient-independent seizure identification by use of a multi-patient trained generic Support Vector Machine (SVM) classifier. The SVM classifier is operates on a large feature vector combining features from a wide variety of signal processing and analysis techniques. The method operates sufficiently accurately to be suitable for use in a clinical environment. The method may also be combined with additional classifiers, such a Gaussian Mixture Model (GMM) classifier, for improved robustness, and one or more dynamic classifiers such as an SVM using
(Continued)

sequential kernels for improved temporal analysis of the EEG signal.

19 Claims, 4 Drawing Sheets

(51) Int. Cl.
*A61B 5/0476* (2006.01)
*G06K 9/00* (2006.01)

(58) Field of Classification Search
USPC .................................................. 600/544, 545
See application file for complete search history.

(56) References Cited

U.S. PATENT DOCUMENTS

| | | | | |
|---|---|---|---|---|
| 6,167,298 | A * | 12/2000 | Levin | 600/545 |
| 7,269,455 | B2 * | 9/2007 | Pineda | 600/544 |
| 7,418,290 | B2 * | 8/2008 | Devlin et al. | 600/544 |
| 2003/0135128 | A1 * | 7/2003 | Suffin et al. | 600/544 |
| 2003/0166996 | A1 * | 9/2003 | Kim et al. | 600/300 |
| 2006/0111644 | A1 * | 5/2006 | Guttag et al. | 600/544 |
| 2007/0185697 | A1 * | 8/2007 | Tan et al. | 703/11 |
| 2008/0167570 | A1 * | 7/2008 | Lithgow | 600/544 |
| 2008/0183097 | A1 * | 7/2008 | Leyde et al. | 600/545 |
| 2008/0234598 | A1 * | 9/2008 | Snyder et al. | 600/545 |
| 2009/0082689 | A1 * | 3/2009 | Guttag et al. | 600/544 |

OTHER PUBLICATIONS

Meng et al. Gaussian mixture models of ECoG signal features for improved detection of epileptic seizures. Medical Engineering and Physics 26 (2004) 379-393.*

Chaovalitwongse W A et al: "On the time series support vector machine using dynamic time warping kernel for brain activity classification" Cybernetics and Systems Analysis, vol. 44, No. 1, Jan. 1, 2008 (Jan. 1, 2008), pp. 125-138.

Gonzalez-Vellon B et al: "Support vector machines for seizure detection" Proceedings of the 3rd IEEE International Symposium on Signal Processing and Information Technology, ISSPIT 2003, Dec. 14, 2003 (Dec. 14, 2003), pp. 126-129.

Shoeb A et al: "Patient-specific seizure onset detection" Epilepsy and Behavior, vol. 5, No. 4, Aug. 1, 2004 (Aug. 1, 2004), pp. 483-498.

Thomas E M et al: "A comparison of generative and discriminative approaches in automated neonatal seizure detection" WISP 2009, 6th IEEE International Symposium on Intelligent Signal Processing, Aug. 26, 2009 (Aug. 26, 2009), pp. 181-186.

Yang J .et al: "Why can LDA be performed in PCA transformed space?" Pattern Recognition, vol. 36, No. 2, Feb. 1, 2003 (Feb. 1, 2003), pp. 563-566.

Faul S et al: "Age-independent seizure detection". 31st Annual International Conference of the IEEE EMBS, Sep. 3, 2009, pp. 6612-6615.

Chua K C et al: "Automatic identification of epileptic electroencephalography signals using higher-order spectra." Proceedings of The Institution of Mechanical Engineers. Journal of Engineering in Medicine, vol. 223, May 2009, pp. 485-495.

\* cited by examiner

METHOD FOR THE REAL-TIME IDENTIFICATION OF SEIZURES IN AN ELECTROENCEPHALOGRAM (EEG) SIGNAL

INTRODUCTION

The present invention relates to a method for the real-time identification of seizures in an Electroencephalogram (EEG) signal.

The brain is the most complex organ of the human body and further understanding of its function represents a great challenge in the areas of medicine, biomedical engineering and informatics. Brainwaves are generated by neural sources within the brain and propagate a measurable electromagnetic field onto the scalp. The resulting Electroencephalogram (EEG) provides a non-invasive measurement of brain electrical activity, which can be measured using surface electrodes and a recording device. For example, the placement of these electrodes may be governed by the international 10-20 system of electrode placement. Each channel of EEG data is made up by combining the signals from two electrodes. The electrodes are usually paired in either a bipolar montage or a referential montage. In the bipolar montage, a channel is made by referencing each electrode with one other electrode, which may then be used as the reference electrode for the next channel and so on until a chain of electrode pairs is built up. In the referential montage, each channel is built up by referencing each electrode to one common reference electrode. The reference electrode may be placed on either a non-cerebral site, such as linked earlobes; an area of the head deemed to be relatively electrically quiet; or made up from an average of all the electrodes. The resulting signals are converted to digital values and then generally fed to the front-end of an EEG recording system. The EEG shows seemingly random activity in the p-volt range.

The EEG differs greatly for different age groups, with the EEG of neonates in particular being significantly different to that of older children and adults. The EEG of the neonate is unique. Patterns of brain activity are seen in this period that mirror the rapid maturational changes taking place in the brain. Waveforms appear in the EEG data that are not present at any other time of life. Sleep states are varied, change rapidly and are very different from those seen in older children and adults.

The occurrence of seizures in full term neonates is most commonly seen in encephalopathy, stroke, infection and haemorrhage. It is very difficult to detect seizures in neonates as they do not always exhibit obvious behavioural change during a seizure. However, it is important that neonatal seizures are detected as failure to detect seizures and the resulting lack of treatment can result in brain damage and in severe cases, death. Currently, the only suitable method for detecting all seizures in neonates is to use a dedicated monitor which records the electrical activity of the brain which must then be analysed by an expert in the field. If the necessary hardware and expertise are unavailable, neonatal seizures will in general go undiagnosed.

Older children and adults can experience generalised seizures wherein the whole brain is affected by brain cell malfunction and the patient may lose consciousness. Tonic-clonic seizures and Absences are examples of generalised seizures. A Tonic-Clonic seizure is a major convulsive seizure where, in the tonic phase, the body stiffens briefly, and in the clonic phase, starts jerking. An Absence looks like a short staring spell that lasts for a few seconds. This type of seizure is most often seen in children. In order to correctly diagnose and subsequently treat seizures in older children and adults, it is necessary to examine the EEG relating to the seizure, in particular the temporal aspects of the seizure, such as the duration of the different phases of seizure and other such characteristics. In this way, the type of seizure can be identified accurately.

Therefore, the detection of seizure events is the most important requirement in neonates while detection and temporal precision of the detection is important in adults. However, given the significant differences between EEG data for neonates and that of adults and older children, there is no known single method that can analyse any EEG signal so as to provide both the detection of the majority of seizure events and precise details of those events once detected. Therefore dedicated neonatal or adult systems must be used, increasing the cost of EEG monitoring for a medical facility.

Throughout the specification, the term 'real-time' is used to refer to the operation of a method wherein the method can process the data as fast or faster than the data is collected.

It is an object therefore of the present invention to provide a method of analysing EEG data that overcomes at least some of the above-mentioned problems.

SUMMARY OF PRIOR ART

The paper "Classifier models and architectures for EEG based neonatal seizure detection" (Greene, B. R., Marnane, W. P., Lightbody, Reilly, R. B. and Boylan, G. B. *Physiological Measurement*, Vol. 29, No. 10, pp. 1157-1178, October 2008) explores some of the classification types and configurations which can be used for neonatal seizure detection. It describes testing a linear discriminant, quadratic discriminant and regularised discriminant classifier on a neonatal seizure dataset. It also compares early integration, wherein all features from the multiple channels of EEG data are passed into one classifier; and late integration, wherein each channel of EEG data is classified separately; as well as bipolar and referential montages. A montage refers to the representation of EEG channels. The early integration, regularized discriminant system performed was the best performing system in these tests.

The paper "A comparison of quantitative EEG features for Neonatal Seizure Detection" (Greene, B. R., Faul, S., Marnane, W. P., Lightbody, G., Korotchikova, I. and Boylan, G. B., Clinical Neurophysiology Vol. 119, No. 6, pp. 1248-1261, June 2008.) examined twenty one frequency, time, modelling and entropy features and used standard statistics to determine which feature had the most significant change from non-seizure to seizure. RMS amplitude, the number of max and min and the autoregressive model fit were the top performing features, and a combined system utilising a linear discriminant classifier gave a Receiver Operator Characteristic (ROC) area of 0.89 (81.75% accuracy over all epochs).

The paper "Gaussian Process Modelling of the Neonatal EEG for the Detection of Seizures" (Faul, S., Gregorcic, G., Boylan, G. B., Connolly, S., Marnane, W. P. and Lightbody, G., IEEE Transactions on Biomedical Engineering, Vol. 54, No. 12, pp. 2151-2162, December 2007.) explored the use of Gaussian process modelling with neonatal EEG. This technique has previously been employed in control systems. Two features of the Gaussian model, namely the hyperparameter ratio and the prediction variance were developed to estimate the level of structure in the EEG, indicative of seizure. The measures were compared with ten other EEG measures and tested on a neonatal database. Mutual information and a neural network classifier were used to measure the performance of each measure, with the prediction variance performing the best of all measures and the hyperparameter ratio having the 7$^{th}$ best performance.

The paper "An Evaluation of Automated Neonatal Seizure Detection Methods" (Faul, S., Boylan, G. B., Connolly, S., Marnane, W. P. and Lightbody, G., "An Evaluation of Automated Neonatal Seizure Detection Methods", Clinical Neurophysiology, Vol. 116, No. 7, pp 1533-1541, July 2005.) discusses the three best known, previously developed neonatal seizure detection algorithms. The Gotman, Liu and Celka algorithms were implemented and tested for the first time on the same EEG database. Improvements to each algorithm were suggested and tested. The algorithms' performance on the database showed that while each algorithm has its particular strengths, none proved accurate enough for clinical use.

The paper "Automated Single Channel Seizure Detection in the Neonate" (Greene, B. R., Boylan, G. B., Marnane, W. P., Lightbody, G., Faul, S. and Connolly, S., 30th Annual IEEE International Conference of the Engineering in Medicine and Biology Society EMBS 2008, 20-24 Aug. 2008.) takes some of the work previously carried out on multi-channel EEG and examines the potential performance on a single EEG channel. The C3-C4 channel proved to hold the most information regarding seizure activity. Extracting 7 features and using a regularised discriminant classifier gave an average good detection rate of 84% with a false detection rate of 10.5%.

The paper "Characterisation of Heart Rate Changes and their Correlation with EEG During Neonatal Seizures" (Doyle, O. M., Greene, B. R., Marnane, W. P., Lightbody, G. and Boylan, G. B., 30th Annual IEEE International Conference of the Engineering in Medicine and Biology Society EMBS 2008, 20-24 Aug. 2008.) investigated the correlation between instantaneous heart rate data obtained from ECG and the RMS amplitude of the EEG in neonates during seizure events. A QRS detector was used to estimate the instantaneous heart rate and correlation between this and the RMS amplitude was calculated for each event. Correlations were confirmed between the heart rate and RMS amplitude in either baseline, pre-seizure, seizure or post-seizure data for every seizure. This work confirms that the ECG could be a useful aid to EEG seizure detection.

The paper "Seizure Detection in Neonates: Improved Classification through Supervised Adaptation" (Thomas, E. M., Greene, B. R., Lightbody, G., Marnane, W. P. and Boylan, G. B., 30th Annual IEEE International Conference of the Engineering in Medicine and Biology Society EMBS 2008, 20-24 Aug. 2008.) describes an adaptive classifier which is primarily trained on data from a large dataset, but which then adapts to the test patient using a learning algorithm which optimises the classifier over a small number of datapoints from the test patients EEG. This creates an adapted classifier which retains the generalisation properties of the global classifier yet is designed specifically for the test patient. Three different learning schemes are presented. Overall, positive improvements in classification are found, but in some patients performance is reduced.

The paper "Seizure Detection in Neonates using Discriminant Analysis" (Thomas, E. M., Lightbody, G., Marnane, W. P., Greene, B. R., and Boylan, G. B., IET Irish Signals and Systems Conference 2007, Derry, 13-14 Sep. 2007, pp 37-42.) presents a comparison of linear discriminant and quadratic discriminant models for classification. Seventeen frequency, time and information theory domain features are extracted from single-channel EEG. A number of feature normalising schemes are also compared. The linear discriminant classifier with an unweighted normalised feature vector resulted in the best performance, with an ROC area of 0.79.

The paper "The effect of frequency band on quantitative EEG measures in neonates with Hypoxic-ischaemic encephalopathy" (Doyle, O. M., Greene, B. R., Murray, D. M., Marnane, W. P., Lightbody, G. and Boylan, G. B., 29th Annual IEEE International Conference of the Engineering in Medicine and Biology Society EMBS 2007, 22-26 Aug. 2007, pp. 717-721.) describes the extraction of three features from the EEG, namely spectral edge frequency, spectral entropy and relative power, for 4 different frequency bands of the EEG. The performance of the measures for each frequency band are compared to establish if these measures might be able to predict the long-term outcome of the neonate. The use of different frequency bands had a notable effect on each measure. No band stands out as being the optimum band to use for outcome prediction. The optimal frequency band is dependent on the measure being used. It is also concluded that the EEG activity in the 0-1 Hz range may carry important clinical information.

The paper "Gaussian Process Modelling as an Indicator of Neonatal Seizures" (Faul, S., Boylan, G. B., Connolly, S., Marnane, W. P. and Lightbody, G., "Gaussian Process Modelling as an Indicator of Neonatal Seizures," The Third IASTED International Conference on Signal Processing, Pattern Recognition and Applications SPPRA2006, February 15-17 2006, Innsbruck, Austria, pp. 177-182.) describes the development of the Gaussian process modeling measures for the first time for use with EEG. Two indicative measures are obtained from the constantly retrained model, namely the hyperparameter ratio and the prediction variance. A comparison is performed with a newly developed autoregressive modeling approach and another 20 EEG features. Feature selection is performed using the Mutual Information Exclusion Function which ensures that each chosen feature adds additional information about seizure events. Both Gaussian process model features were selected in the top three, showing that they provide useful information about seizure events and that they each contain information that the other does not.

The paper "A Novel Automatic Neonatal Seizure Detection System" (Faul, S., Boylan, G. B., Connolly, S., Marnane, W. P. and Lightbody, G., IEE Irish Signals and Systems Conference 2005, pp. 377-382, September 2005.) discusses the framework for a new seizure detection system, addressing the problems discovered in implementing previous neonatal seizure detection systems. This system comprises of an artifact removal system based on Independent Component Analysis, a number of features including entropy, wavelet, modeling and chaos theory measures, a normalization routine based on probability and neural network. For this test 10 hours of single-channel EEG was used for testing. Sensitivity of 69% and specificity of 92% was achieved.

The paper "Chaos Theory Analysis Of The Newborn EEG—Is It Worth The Wait?", (Faul, S., Boylan, G. B., Connolly, S., Marnane, W. P. and Lightbody, G., IEEE International Symposium on Intelligent Signal Processing (WISP2005), pp. 381-386, Faro September 2005.) examines a number of chaos (or nonlinear dynamic systems) theory measures for use with EEG. In general, these features take a considerable amount of time to compute as they have to build up an attractor of a system given by time delay embedding. The analysis compared a number of information theory measures with the chaos theory measures. The chaos theory measure with the best performance was the Kaplan-Yorke dimension which provides similar information to the highly performing information theory measure of entropy. However, given that the KY dimension required a computation time of approx 1000 times that of the entropy, its inclusion, and indeed that of the lesser performing chaos theory measures, in a seizure detection system is not warranted.

The paper "A Method for the Blind Separation of Sources for use as the First Stage of a Neonatal Seizure Detection" (Faul, S., Boylan, G. B., Connolly, S., Marnane, W. P. and Lightbody, G., IEEE International Conference on Acoustics, Speech, and Signal Processing, Vol. 5, pp. 409-412, March 2005.) discusses artifacts and the resulting problems caused to seizure detection systems. Often they may mimic or obscure seizure waveforms in the EEG. Independent Component Analysis is a method of splitting up a number of signals into statistically independent sources. In this fashion, EEG can be split up into seizure, non-seizure and artifact components. The difficulty is in determining which sources contain important seizure information and which sources can be discarded as artifact or noise. A method of complexity analysis is developed here in which sources are ordered and selected based on the structure and consistency therein. The system successfully selected those sources containing seizure information and allowed data reduction of approx 70% in most cases and 30% in the worst case.

The paper "Computer Aided Seizure Detection in Newborn Infants" (Faul, S., Boylan, G. B., Connolly, S., Marnane, W. P. and Lightbody, G., IEE Irish Signals and Systems Conference 2004, pp. 428-433, June-July 2004.) compared the performance of 3 well-known, previously developed neonatal seizure detection systems. While each algorithm had its strengths and engineering merits, none exhibited the levels of performance required in a clinical setting. 117 hours of 12 channel EEG data from 15 patients was used for algorithm testing.

U.S. Pat. No. 6,735,467 "Method and System for Detecting Seizures using Electroencephalogram." in the name of Wilson describes a method of detecting epileptic seizures in multi-channel EEG. The method employs matching pursuit, a time-frequency measure, to decompose each epoch of data into subcomponents. Neural networks, incorporating some expert knowledge, are then used to classify the subcomponents. The results are then smoothed. This patent describes the method for use as part of an offline processing tool and does not disclose a solution for real-time, online function. Also, only features extracted using time-frequency measures are used to describe the EEG signal. Additionally, no artifact removal techniques are discussed.

International Patent Application Publication No. WO/2008/058343 "A method for detecting EEG seizures in a newborn or a young child" in the name of University of Queensland et al describes a system for detecting seizures in newborns. A matching pursuit is used to search for short-term, high amplitude activity which is classed as artifact. A time-frequency representation is then computed and peaks are detected and linked. A number of features are then calculated from this. All features have to be in seizure state for a seizure to be recognised. A collection of simple thresholds are used for classification.

Both U.S. Pat. No. 6,735,467 and WO/2008/058343 are specific to either neonatal or epileptic seizures. Neither describes a method for characterising artifact and non-seizure EEG—they are simply classified as one or more types of seizure or non-seizure. Both disclosures are restricted in feature choice to simple time, frequency and time-frequency domain features and do not discuss the possible use of other features to be extracted from the signal.

The paper "Patient-specific seizure onset detection system" (Shoeb, A. Edwards, H. Connolly, J. Bourgeois, B. Treves, T. Guttag, J., Epilepsy & Behaviour, v5, 2004.) describes the application of Support Vector Machines (SVMs) as a classifier for patient-specific detection of seizures in adults. The SVM models were trained with fixed machine hyper-parameters. Two configurations were investigated: a spatially independent configuration, where models are trained per channel; and a spatially dependent configuration where a single model is trained based on the concatenated feature vectors from each channel.

The paper "Gaussian mixture models of ECoG signal features for improved detection of epileptic seizures" (L. Meng, M. Frei, I. Osorio, G. Strang, T. Nguyen, Medical Engineering & Physics, Volume 26, Issue 5, 2004.) describes the use of Gaussian Mixture Model (GMM) classifiers for seizure detection.

The papers "On the time series support vector machine using dynamic time warping kernel for brain activity classification" (W. A. Chaovalitwongse, P. M. Pardalos, Cybernetics and Systems Analysis, 2008.); "Comparison of Sequence Discriminant Support Vector Machines For Acoustic Event Classification" (A. Temko, E. Monte, C. Nadeu, IEEE International Conference on Acoustics, Speech, and Signal Processing, 2006); "Electroencephalogram processing using Hidden Markov Models" (D. Novak, T. Al-ani, A. Hamam, L. Lhotska); and "A Stochastic Framework for Evaluating Seizure Prediction Algorithms Using Hidden Markov Models" (Stephen Wong, Andrew B Gardner, Abba M Krieger, Brian Litt, J Neurophysiol, Vol. 97, No. 3, 2007.) discuss the detection of seizures by means of analysis of temporal evolution and sequentiality of the observed signals. Hidden Markov Models (HMMs) have been applied to EEG in Novak for Brain Computer Interfaces and in Wong for temporal post-processing of the binary decisions via transition matrix design. One sequential kernel based on dynamic time warping has been used for seizure detection in Chaovalitwongse.

U.S. Pat. No. 4,188,956 "Method for the analysis, display and classification of multivariate indices of brain function—a functional electrophysiological brain scan" in the name of John, describes a system which examines EEG and extracts some information. However, the system is not a seizure detection system, it just gathers information from the EEG. The proposed system includes the extraction of information from the background EEG to aid the clinician in treating patients in which seizures are detected. Thus it adds a clinical information element to previous seizure detection systems.

The paper "Principal-Component Localization of the Sources of the Background EEG" (A. C. K. Soong and Z, J. Koles, IEEE Transactions on Biomedical Engineering, Vol. 42, No. 1, pp. 59-67, 1995.) describes a method of localising the source of activity in background EEG. As with U.S. Pat. No. 4,188,956, it is not used as part of a seizure detection system.

STATEMENTS OF INVENTION

According to the invention there is provided a method for the real-time identification of seizures in an Electroencephalogram (EEG) signal, the steps of the method comprising:
(a) receiving an EEG signal comprising at least one channel of EEG data;

(b) for each channel, segmenting the data into a sequential epochs, each epoch having an overlap with its neighbouring epochs;

and for an initial epoch (c) extracting features from the constituent channels;
(d) generating a feature vector from the extracted features;
(e) passing the feature vector through a multi-patient trained generic Support Vector Machine (SVM) classifier and generating an SVM channel seizure output;
(f) fusing the SVM channel seizure outputs for all channels thereby generating an SVM epoch seizure output;
(g) repeating steps (d) to (f) for each subsequent epoch thereby generating a sequence of SVM channel seizure outputs and SVM epoch seizure outputs.

The term 'multi-patient trained generic SVM' is understood to refer to an SVM classifier trained on EEG data representing all seizure types, over all channels and over all patient types, including children and neonates. In this way, the method of the invention provides patient independent, real-time seizure detection in a manner that is sufficiently accurate and reliable to be used in a clinical setting, without requiring the presence of a highly-skilled neurologist. The use of an SVM classifier allows for the use of large feature vectors thereby allowing the classifier to be trained on a wide array of patient data, in turn allowing the classifier to operate in a patient-independent manner. Importantly, the patient independence allows for use of the method of the invention on patients ranging from neonates through to adults, and eliminates the prior art requirement for training the classifier on a specific patient before seizure detection can begin. Including an overlap of epochs ensures all data, including that at the extremes of each epoch, is completely included in processing. Furthermore, the method of the invention provides strong seizure classification accuracy as well as strong seizure temporal onset and offset results, thereby providing the more important and useful clinical data for both neonates and adults. Having been tested on extensive adult and neonatal datasets, the proposed method has demonstrated significantly improved performance over previous methods, with an increase in the number of correctly detected seizures and a reduction in false alarms.

In one embodiment of the invention there is provided a method comprising the additional steps of generating a reduced feature vector; passing the reduced feature vector through a multi-patient trained Gaussian Mixture Model (GMM) classifier and generating a GMM channel seizure output. The term 'multi-patient trained generic GMM classifier' is understood to refer to an GMM classifier trained on EEG data representing all seizure types, over all channels and over all patient types, including children and neonates. In this way, further classification of the channels of the EEG signal may be obtained.

In another embodiment of the invention there is provided a method comprising the additional step of combining the SVM channel seizure output and GMM channel seizure output for each epoch thereby generating a combined channel seizure output. In this way, improved seizure detection results are obtained, as the combination of diverse classifiers will provide improved results over the use of a single classifier. Furthermore, the combination of the SVM and GMM classifiers provides for increased robustness of the overall classification.

In a further embodiment of the invention there is provided a method comprising the additional step of fusing the combined channel seizure outputs for an epoch across all channels thereby generating a combined epoch seizure output for each epoch. In this way, a classification with improved accuracy is provided by the combined epoch seizure output.

In one embodiment of the invention there is provided a method in which the step of generating a reduced feature vector comprises using Principal Component Analysis (PCA) to generate a decorrelated feature vector, and subsequently using Linear Discriminant Analysis (LDA) on the decorrelated feature vector to generate the reduced feature vector. In this way, the PCA provides a feature vector comprising a number of features having a high information content and features have less information content, including some features which containing very little relevant information. The subsequent application of the LDA removes those features from the feature vector that contain little useful information. Further information on this technique can be found in J. Yang and J. yu Yang, "Why can LDA be performed in PCA transformed space?" Pattern Recognition, vol. 36, no. 2, pp. 563-566, 2003.

In an alternative embodiment of the invention there is provided a method comprising the additional step of converting each channel seizure output into a binary channel seizure decision. In this way, the channel seizure output value generated by the classifier is converted, by way of a binary decision, to one of two options—seizure or non-seizure.

In one embodiment of the invention there is provided a method in which the channel seizure output comprises a numerical value and the step of converting the channel seizure output into a binary channel seizure decision is based on the sign of the numerical value. The output of the multi-patient trained generic SVM classifier for each channel, that is the channel seizure output, comprises a numerical value, wherein the sign of that value represents the one of two classification options for that SVM, and the magnitude of the channel seizure output represents the confidence in the classification decision. The sign of the channel seizure output is therefore a very useful manner of providing the binary decision.

In another embodiment of the invention there is provided a method in which the channel seizure output comprises a numerical value, the magnitude thereof indicating the confidence level of the channel seizure output; and the step of converting each channel seizure output into a binary channel seizure decision comprises making the binary decision based on the confidence level of the channel seizure output. In this way, the sensitivity of the seizure detection can be adjusted based on the confidence that a seizure has been detected. For example, the method may be implemented such that the binary channel seizure decision indicates a seizure only if the classifier is at 75% confident in the decision it has made regarding the presence of a seizure in that epoch of that channel.

In a further embodiment of the invention there is provided a method comprising the intermediate step of the user selecting the confidence level to be used in the binary decision. In this way, a clinician may adjust the sensitivity of the seizure detection in a case by case manner, depending on the requirements of the test in question.

In another embodiment of the invention there is provided a method in which the method comprises the additional step of converting each channel seizure output to a normalised probabilistic value between 0 and 1. The provisional of a normalised value in this manner allows for convenient further processing of the channel seizure output data. Furthermore the use of the normalised probabilistic value between 0 and 1 is very useful for clinical staff, allowing them to quickly evaluate patient condition.

In an alternative embodiment of the invention there is provided a method in which the step of fusing the channel seizure outputs thereby generating an epoch seizure output comprises fusing the channel seizure decisions thereby generating an epoch seizure decision. In this way, the epoch seizure decision represents a decision as to whether the epoch in question contains seizure activity.

In a further embodiment of the invention there is provided a method in which the step of fusing the channel seizure outputs comprises using a logical OR operator. This is particularly efficient way of fusing the channel seizure outputs resulting in an epoch in which a seizure has been detected in just one channel thereof will be classified as a seizure epoch. This provides improved accuracy in detecting localised seizures that only affect one channel of the EEG signal.

In a further embodiment of the invention there is provided a method in which the method comprises the initial step of applying data reduction techniques to the EEG signal. In this way, the processing load for the subsequent steps of the method is reduced.

In an alternative embodiment of the invention there is provided a method in which the data reduction techniques comprise down-sampling the EEG signal. EEG data is typically sampled at 256 Hz, however the method of the invention will operate to provide clinical standard results if the data sampled at 256 Hz is down sampled by a factor of 8 to 32 Hz. Reducing the sampling frequency greatly reduces the processing time and power required to provide useful results.

In one embodiment of the invention there is provided a method in which the data reduction techniques comprise bit-width reduction of the EEG signal. Typically, EEG data is recorded at 16 to 32 bits per sample; however the method of the invention will provide clinical standard results with each sample reduced to 12 bits per sample. This greatly reduces the processing load of the method of the invention, allowing faster operation.

In another embodiment of the invention there is provided a method comprising a pre-processing step of performing spectral subtraction on the EEG signal. In this way, the amount of additive noise in the EEG signal, such as that due to the external surroundings in which the EEG data is recorded and noise introduced by the measurement equipment, is reduced.

In a further embodiment of the invention there is provided a method in which the step of performing spectral subtraction on the EEG signal comprises carrying out the following steps
  computing an average frequency spectrum of non-seizure EEG signal over a period of time to estimate the noise frequency spectrum;
  transforming the EEG signal into the frequency domain;
  subtracting the average frequency spectrum from the EEG frequency spectrum;
  calculating phase information for the EEG signal;
  combining the result of the subtraction with the phase information;
  transforming the combination of the result of the subtraction and the phase information back to the time domain, providing a noise-reduced EEG signal. This is a particularly effective way of providing spectral subtraction in the method of the invention.

In an alternative embodiment of the invention there is provided a method comprising a pre-processing step of standardising the EEG signal using montage elimination techniques. As different clinicians prefer different EEG recording montages, errors and inconsistencies can be introduced into the EEG data at this stage. Furthermore, the use of montage elimination allows training and application of the method of the invention independently of the montage used to record the EEG data. This greatly increases the versatility of the method of the invention.

In one embodiment of the invention there is provided a method in which the montage elimination techniques comprise applying Independent Component Analysis (ICA) to the EEG signal. Each montage used in recording EEG is essentially a different mixing of the EEG sources recorded at the electrodes. In this way, the ICA algorithm can separate the EEG signal into a set of sources independent of the montage used to record them.

In another embodiment of the invention there is provided a method comprising the pre-processing step of applying Non-negative Matrix Factorisation (NMF) of the EEG signal. NMF is designed to describe signals by their constituent parts. As the EEG signal itself can be regarded as combination of parts, such as non-seizure, seizure, artifact and noise, NMF is useful for identifying and assisting in the removal of noise and artifacts in the EEG signal.

In a further embodiment of the invention there is provided a method comprising the additional step of applying a moving average filter to the sequence of epoch seizure outputs. In this way, random noise can be reduced while maintaining a sharp step response thus helping to avoid the seizure decision labels alternating too frequently.

In another embodiment of the invention there is provided a method in which the moving average filter uses a rectangular window function having a filter order of 15 epochs. These settings provide for efficient performance from the moving average filter.

In one embodiment of the invention there is provided a method comprising the additional step of applying a collar technique to the sequence of epoch seizure decisions. In this way, the sequence of epochs representing a seizure is lengthened at each end to include epochs classified as non-seizure, as these epochs may contain information relevant to the development of the seizure over time. The use of the collar technique compensates for the difficulties in detecting pre-seizure and post-seizure details in the EEG and increases the temporal accuracy of seizure detection.

In a further embodiment of the invention there is provided a method in which each epoch is approximately 8 seconds in duration. For EEG data recorded at 256 Hz, an 8 second epoch corresponds to 2048 samples (before any down-sampling occurs), and for EEG data recorded at 250 Hz, 8.2 seconds corresponds to 2048 samples. Clinically, a seizure must last at least 10 seconds to be defined as a seizure, by choosing an epoch length of approximately 8 seconds, it is ensured that there will be enough seizure EEG data present in an epoch to ensure it is correctly classified as a seizure epoch.

In an alternative embodiment of the invention there is provided a method in which each epoch overlaps its neighbouring epochs by 50%. In this way, it is further ensured that if a seizure occurs that it will take up sufficient time in at least one epoch to ensure that a seizure is identified by the classifier. The duration of the epoch and percentage overlap may be varied, along with the characteristics of the Moving Average Filter and the window applied by the collar technique so as to provide optimum results. Changes in the epoch duration and overlap would require adjustment of the characteristics of the Moving Average Filter and collar technique.

In one embodiment of the invention there is provided a method in which the step of extracting features from the constituent channels comprises extracting features using speech recognition analysis techniques. The application of certain speech recognition analysis techniques to EEG signals has provided further features that may be extracted from the EEG channels, and those features have proved useful in the classification of seizures. This is believed to be due to the similarities between the EEG signals and speech signals, if the convolutive analysis of EEG is considered in the same way as it is done for speech. The EEG can be thought as a result of brain signals convoluted with scalp/head response in the same way as speech may be considered to be audio signals convoluted with acoustical environment response in speech recognition techniques.

In another embodiment of the invention there is provided a method in which the speech recognition analysis techniques comprise one or more of mel-frequency cepstrum, fundamental frequency and modulation frequency. These are particularly useful features to be extracted from the EEG signal as they have a high spectral information content, provide a good spread of information content from the spectrum, and provide useful results when used as part of the feature vector to train the classifiers and subsequently classify seizures in the EEG signal.

In an alternative embodiment of the invention there is provided a method in which the speech recognition analysis techniques comprise one or more of the first and second derivatives of mel-frequency cepstrum, fundamental frequency and modulation frequency.

In a further embodiment of the invention there is provided a method in which the speech recognition analysis techniques comprise one or more of linear prediction analysis; linear prediction cepstral coefficients; perceptual linear predictive analysis; Rasta-PLP; frequency filtering; and first and second time derivatives of these features. These features provide further useful information on the EEG signal.

In a further embodiment of the invention there is provided a method in which the step of extracting features from the constituent channels comprises extracting features using time domain analysis techniques. In this way, useful information may be extracted from the EEG data.

In an alternative embodiment of the invention there is provided a method in which the step of extracting features from the constituent channels comprises extracting features using frequency domain analysis techniques. In this way, useful information may be extracted from the EEG data.

In one embodiment of the invention there is provided a method in which the step of extracting features from the constituent channels comprises extracting features using time-frequency analysis techniques. In this way, useful information may be extracted from the EEG data.

In another embodiment of the invention there is provided a method in which the step of extracting features from the constituent channels comprises extracting features using information theory analysis techniques. In this way, useful information may be extracted from the EEG data.

In a further embodiment of the invention there is provided a method in which the step of extracting features from the constituent channels comprises extracting features using nonlinear dynamics system theory analysis techniques. In this way, useful information may be extracted from the EEG data.

In an alternative embodiment of the invention there is provided a method in which the step of extracting features from the constituent channels comprises extracting features using data modelling techniques. In this way, useful information may be extracted from the EEG data.

In one embodiment of the invention there is provided a method in which the step of extracting features from the constituent channels comprises extracting the Kullback-Leibler distance feature. In this way, useful information may be extracted from the EEG data.

In another embodiment of the invention there is provided a method in which the step of extracting features from the constituent channels comprises extracting the Kolmogorov complexity feature. In this way, useful information may be extracted from the EEG data.

By combining features from a wide variety of different signal processing areas, such as those mentioned above, a large amount of information from the EEG signal is obtained, covering many aspects of the EEG signal, thereby allowing improved training of the classifiers and improved seizure identification in use.

In a further embodiment of the invention there is provided a method in which the step of extracting features from the constituent channels comprises extracting forty-five or more features. In this way, a large feature vector is obtained, which provides information on the EEG signal from a wide variety of aspects. This provides for a well trained classifier that provides highly accurate results in use. The use of a large feature vector does not hinder the operation of the SVM classifier, either during the training phase or in use. The use of a large feature vector, generated by extracting forty-five or more features from the EEG signal, allows many aspects of the seizure to be captured in the feature vector, and further allows compensation for certain seizure types that may not manifest in the more well-known seizure analysis features. For example, a particular feature may detect the majority of seizures, but it will not always identify if a seizure is present. However, in those situations, it is highly likely that another feature that does not provide useful information in more common seizures, will in this case detect the seizure.

In an alternative embodiment of the invention there is provided a method in which the step of extracting features from the constituent channels comprises extracting fifty-five or more features. Again, an even larger feature set will provide improved results by including further features that contain useful information relating to the EEG signal.

In one embodiment of the invention there is provided a method in which in which the step of extracting features from the constituent channels comprises extracting eighty-five or more features. In a particularly preferred implementation, eighty-six features are extracted and used to form the feature vector. Such an implementation provides highly accurate seizure identification results.

The use of a large feature vector, that is a feature vector comprising upwards of forty-five features, with those features having been extracted using techniques from a wide variety of signal processing and analysis techniques, provides highly accurate real-time seizure identification.

In a further embodiment of the invention there is provided a method in which the method comprises the additional step of: passing the feature vector through a Support Vector Machine (SVM) with sequential kernels and generating a dynamic SVM channel seizure output. The use of an SVM classifier with sequential kernels provides dynamic classification, in that it recognises sequences of feature vectors, not just individual vectors. This allows the temporal evolution of the EEG signal to be taken into account in seizure detection. For example, an eye blink could in some cases be classified as a seizure, however, it will lack the temporal development of a seizure, and is therefore more likely to be correctly classified if the temporal evolution is considered by the classifier. Sequential SVMs provide information on which specific seizures are most useful in terms of classifying between seizure and non-seizure data, while non-sequential SVMs provide information on which epochs are useful for classifying. Sequential SVMs use a subset of the seizures in the training data which are the most critical for correct classification. The difference between this and the normal SVM is that in the sequential case whole seizures are used to discriminate, whereas in normal SVMs individual epochs are used.

In an embodiment of the invention there is provided a method in which the sequential kernels comprise a dynamic time warping kernel. This is an efficient kernel for use sequentially to provide a dynamic SVM channel seizure output.

In an alternative embodiment of the invention there is provided a method in which the method comprises the additional steps of combining the dynamic SVM classifier channel seizure output for an epoch with any other classifier channel seizure outputs for that epoch, thereby generating a dynamic SVM combined seizure output; and then fusing the dynamic SVM combined seizure outputs for that epoch over all channels thereby generating a dynamic SVM combined epoch seizure output. In this way, improved classification results may be obtained, by providing a result that combines the classification of the dynamic SVM classifier with any other classifiers used in the method.

In an alternative embodiment of the invention there is provided a method in which the epoch seizure outputs are combined using weighted arithmetic mean techniques. In this way, the method of the invention allows the outputs or decisions of each classifier to be weighted as desired. For example, the SVM classifier provides more accurate results than the GMM classifier and will therefore be given a heavier weight if combining results from both classifiers. This reduces the effects of the less accurate results of the GMM classifier on the final results. When correctly combined, the combination of SVM and GMM will always provide improved results over SVM alone.

In an embodiment of the invention there is provided a method further comprising passing the feature vector through a multi-patient trained generic SVM classifier and generating an SCM channel artefact output. In this way the method of the invention may be used to identify artifacts in the EEG signal and provide useful information on those artifacts to the clinician.

In another embodiment of the invention there is provided a method comprising the additional step of applying Viterbi temporal decoding to the sequence of epoch seizure outputs. In this way, temporal information from epoch decisions is included in the decision process, by estimating the sequence of states of the system.

According to the invention there is further provided a computer program product having computer program instructions for causing a computing device to perform the method of the invention.

In an embodiment of the invention there is provided a computer program product stored on a carrier.

In one embodiment of the invention there is provided a computer program product in which the carrier is one of a RAM, a ROM, a floppy disc, a CD, a CD ROM, a DVD, a memory stick, an integrated circuit, an FPGA, or a computer readable medium.

According to the invention there is further provided an EEG machine having memory with a computer program stored thereon having program instructions for causing the EEG machine to perform the method of the invention.

According to the invention there is further provided an apparatus for the real-time identification of seizures in an Electroencephalogram (EEG) signal, the apparatus comprising:
means for receiving an EEG signal comprising at least one channel of EEG data;
means for segmenting the data of each channel into a sequential epochs, each epoch having an overlap with its neighbouring epochs;
and for each epoch
means for extracting features from the constituent channels;
means for generating a feature vector from the extracted features;
a multi-patient trained generic Support Vector Machine (SVM) classifier adapted to process the feature vector so as to generate an SVM channel seizure output;
means for fusing the SVM channel seizure outputs for all channels thereby generating an SVM epoch seizure output.

Such an apparatus is particularly useful for identifying seizures in an EEG signal.

DETAILED DESCRIPTION OF THE INVENTION

The invention will now be more clearly understood from the following description of an embodiment thereof given by way of example only with reference to the accompanying drawings in which:—

Prior to the use of the method of the invention for the real-time detection of seizures in an EEG signal, it is necessary to train the SVM classifier on sets of training EEG data. The training data comprises adult and neonate EEG signals. The training data used consists of EEG data from seventeen neonatal patients and fifteen adult patients. Patients were not selected on any criteria, all available patients having useable data were used so as to maximize the available training data.

The training data set is made up of 132.7 hours of adult EEG containing sixty-two seizures, of total duration of two hours. The training data set further consists of 267.9 hours of neonatal EEG containing 691 seizures of total duration of 54 hours.

Training data is chosen such that artifacts are avoided, by removing any epochs affected by artifacts from the training data set. Also, seizure training data is selected to ensure that it is all descriptive of seizure activity. In this way, epochs comprising unclear data from before or after seizures are removed from the training data.

Non-seizure EEG where the signal is much deteriorated by artifacts are also avoided in the training data set. More common, smaller scale artifacts are not avoided in order that the classifier may correctly classify them during operation.

Training data is annotated on a per-channel basis. If a seizure is localized to one or a number of channels, the data from the channels not involved in the seizure should not be used for training. For example, if the seizure is present in just two channels out of eight, then the other six channels of training data for the seizure epochs is not used for training.

Figure 1:
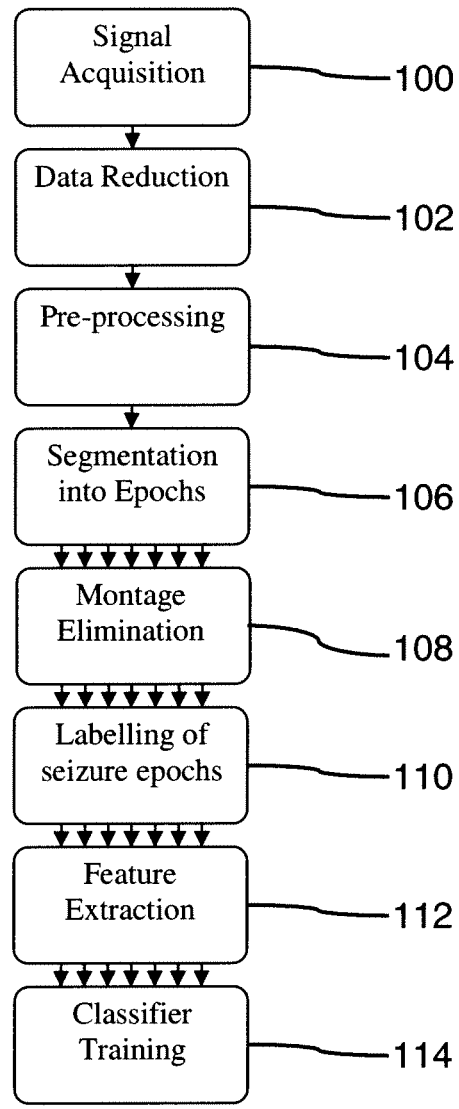
FIG. 1 is a flow chart of training of the Support Vector Machine.

In the training phase, the training EEG data is processed according to the following steps as illustrated in FIG. 1. In step 100, the EEG signal comprising a plurality of channels of data is received. EEG signals are measured from the scalp using electrodes. There may be any number of these channels used in the system, usually in the order of six to twelve.

In step 102 the EEG data is reduced using a number of techniques. In the first data reduction step, the EEG data is down-sampled to a lower sampling frequency. EEG data is normally recorded at 256 Hz, and is down-sampled by a factor of 8 to 32 Hz. Additionally, the EEG data may also be subject to bit-width reduction. Commonly the level of resolution at which EEG is recorded is not required by the method according to the invention in order to achieve accurate seizure detection. The bit-width reduction reduces the EEG data to a lower number of bits per sample through standard quantisation of the EEG signal, for example, in one embodiment, from 32 bits per sample to 12 bits per sample. Bit-width reduction is particularly advantageous if the method is to be implemented in a portable system, as it is useful for reducing power consumption due to decreased processing load throughout the remainder of the system.

In step 104, pre-processing of the EEG data is carried out. Spectral Subtraction can be used to reduce the amount of additive noise in the EEG data if necessary. This noise is caused by external surroundings and the noise from the measurement equipment. An average frequency spectrum of non-seizure EEG data is computed over a period of time to provide an estimate of the noise frequency spectrum. As the EEG data is recorded, it is transformed to the frequency domain. The average noise spectrum is then subtracted from the EEG frequency spectrum. The resultant spectrum and phase information from the original noisy signal are then combined and the result is transformed back to the time domain, resulting in a de-noised EEG signal. This allows the method to be implemented in different clinical or non-clinical environments where adaptive compensation for additive stationary noise may be required.

In step 106, the EEG data is segmented into epochs of a set duration, typically 8 seconds with each epoch having a 50% overlap with neighbouring epochs. The selection of window length and overlap is carried out in relation to the minimum seizure duration, clinically regarded as 10 seconds. With a window length of 8 seconds and an overlap of 50%, a 10 seconds seizure will fill at a minimum 7 seconds of one window, enough to affect the features of that window. The selections made in relation to epoch length and overlap are also connected to those in the post-processing steps of the classifier, such as those used in smoothing the results.

Steps 100 to 106 have been carried out on the EEG data on the combination of channels. In step 108, analysis is carried out on each channel separately.

In step 108, the EEG data is standardized by eliminating the effect of the montage that was used in gathering the EEG data. Independent Component Analysis (ICA) is used to provide this montage elimination. Each montage used in recording EEG is essentially a different mixing of the EEG sources recorded at the electrodes. In this way, the ICA algorithm can separate the EEG signal into a set of sources independent of the montage used to record them. Using standardized EEG data will remove errors introduced by the varying practices of clinicians. Next, complexity measures are applied to detect channels containing noise. Sources containing noise will be detected based on the clustering of complexity measures as detailed in the prior art.

In step 110 each epoch of each channel is manually labelled as either a seizure epoch or a non-seizure epoch, wherein seizure epochs are labelled as −1 and non-seizure epochs are labelled as +1.

Next a Non-negative Matrix Factorisation (NMF) algorithm is applied to each channel as a form of artifact removal. Firstly in the training stage, bases of artifacts, seizure and non-seizure are created from the signal's spectrogram, using the temporal and sparsity constraints defined by applying cross-validation of the training data. The constraints are very important to ensure that the bases capture temporal evolution differences among artifact, seizure and non-seizure classes and that the bases are sparse to ensure that the signal can be decomposed only using the bases of the corresponding class.

Next, in step 112, features are extracted from each epoch of each channel. Such features include features from the frequency domain, time domain, time-frequency domain, information theory, nonlinear-dynamics system theory, modelling approaches, speech recognition techniques and include some or all of the following:

From the Frequency Domain:
power in frequency bands of width 2 HZ from 1 Hz to 12 Hz with 50% overlap, normalised frequency bands powers;
total power (0-12 Hz);
spectral edge frequency (80%, 90%, 95%);
dominant peak frequency.

From Time Frequency Analysis:
the energy in the 5th coefficient of Daubechy 4 wavelet decomposition that corresponds to t1-2 Hz.

From the Time Domain:
curve length, that is, the sum of the absolute distance between successive samples over the epoch.
number of maxima and minima;
RMS amplitude;
Hjorth parameters (activity, mobility, and complexity);
Zero Crossing Rate (ZCR);
ZCR of the first derivative ($\Delta$) and the second derivate ($\Delta\Delta$);
Variance of $\Delta$ and $\Delta\Delta$;
Nonlinear energy, which is an indicator of the spectral content of the signal From Modelling Techniques:
AR modelling error (model order 1-9), this is a measure of the structured content of the signal;
Gaussian hyperparameters: the parameters of a Gaussian process model;
Gaussian variance: A Gaussian process model is trained on the epoch of data and the confidence of a 1 step ahead prediction is calculated. This is a further measure of the structure content in the signal From Statistical Techniques:
Skewness;
Kurtosis.

From Information Theory:
Shannon entropy;
Spectral entropy;
SVD entropy;
Fisher information;
Conditional entropy;

Permutation entropy.

From Nonlinear Dynamics System Theory:

Approximate entropy;

Maximum Lyapunov exponent;

KY dimension: a measure of the spatial distribution of the attractor.

Other Features:

Kullback-Leibler distance, this measures change is the probability density function of the EEG signal;

Kolmogorov complexity.

Additionally, step 112 comprises the use of feature extraction techniques originating in speech recognition theory. These features mostly involve the estimation of the spectrum of the signal and its analysis.

Mel-frequency cepstrum: a representation of the short-term power spectrum of the signal using frequency spacing based on the mel scale, related to human hearing system response. This technique can also be utilised in the pre-processing stage, similarly to the spectral subtraction, to remove convolutive noise arising from the physical attributes of the head. The mel-frequency cepstrum provides fifteen individual features, corresponding to fifteen frequency ranges.

Fundamental frequency (F0): estimation of the fundamental frequency of a signal;

Modulation frequency: based on the premise that the signal is a lower bandwidth process modulating a higher bandwidth carrier. The modulation frequency provides fifteen individual features, corresponding to fifteen frequency ranges.

The combination of all of the features listed above combine to provide an optimal implementation of the method of the invention generating a feature vector consisting of eighty-six features.

Some further features from the speech recognition domain that may also be considered include:

Linear prediction analysis: method for the estimation of power spectra of the signal based on an all-pole filter;

Linear prediction cepstral coefficients: linear prediction coefficients obtained from the above, represented in the cepstrum domain;

Perceptual linear predictive analysis: uses three concepts of the psychophysics of hearing to estimate the spectrum of the signal;

Rasta-PLP: A method similar to the above but which is less sensitive to slow variations in the spectrum;

Frequency filtering: consisting of the decorrelation of log filter bank energies by applying a linear filter in the frequency domain; and First and second time derivatives of the above features.

The features extracted from the training data for the SVM classifier are normalized anisotropically by subtracting the mean and dividing by standard deviation and the obtained normalizing template is then used in the operational phase.

In step 114, the normalised features extracted from each epoch are then fed to train one SVM classifier. The Gaussian kernel is used. To obtain a good model for SVM the optimal hyper-parameters are searched via a grid search over a set of values. 5-fold cross-validation on the training data is applied to search for the optimal Gaussian kernel parameter and generalization parameters C, in the way that four fifths of the training data is used for training while the remaining fifth is used for testing. It is repeated five times until all parts are tested (5-fold CV) per each pair of values of kernel parameter and generalization parameters C and the results are averaged. The pair that gives the best accuracy (averaged over five folds) is taken as optimal. Once the optimal pair of parameters is found, it is used to train the final model on all the training data.

Figure 2:
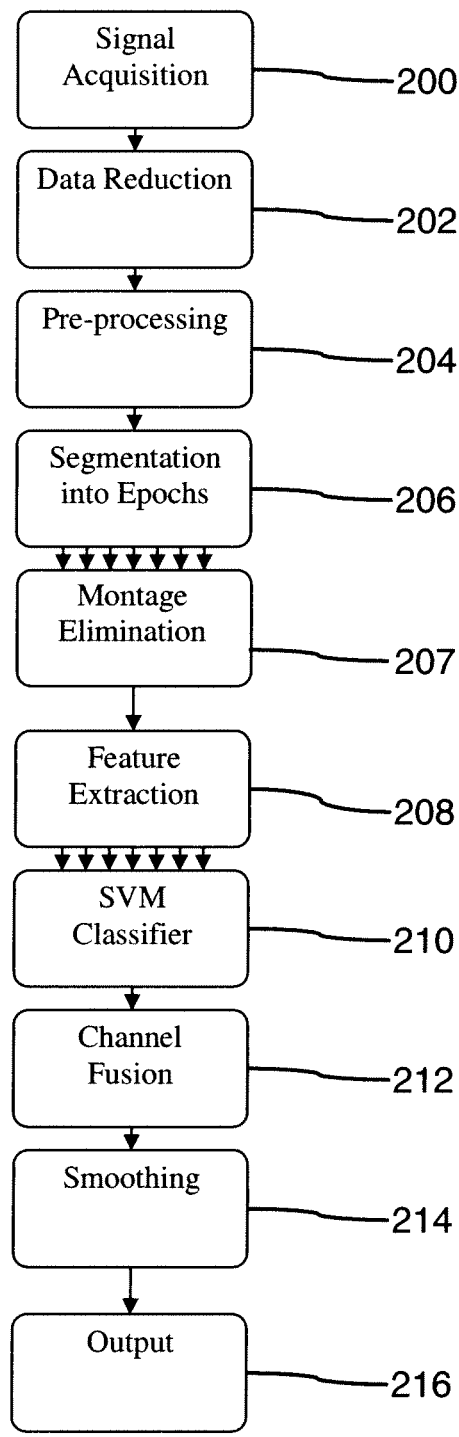
FIG. 2 is a flow chart of the system according to the invention.

Referring to FIG. 2, there is shown a flowchart representing the method of the invention. The initial steps in the method correspond to the initial steps in the training of the SVM classifier, without the annotation steps In step 200, the EEG signal comprising a plurality of channels of data is received. EEG signals are measured from the scalp using electrodes. There may be any number of these channels used in the system, usually in the order of six to twelve.

In step 202 the EEG data is reduced using a number of techniques. In the first data reduction step, the EEG data is down-sampled to a lower sampling frequency. EEG data is normally recorded at 256 Hz, and is down-sampled to 32 Hz. Additionally, the EEG data may also be subject to bit-width reduction. Commonly the level of resolution at which EEG is recorded is not required by the method according to the invention in order to achieve accurate seizure detection. The bit-width reduction reduces the EEG data to a lower number of bits per sample through standard quantisation of the EEG signal, for example, in one embodiment, from 32 bits per sample to 12 bits per sample. Bit-width reduction is particularly advantageous if the method is to be implemented in a portable system, as it is useful for reducing power consumption due to decreased processing load throughout the remainder of the system.

In step 204, pre-processing of the EEG data is carried out. Spectral Subtraction can be used to reduce the amount of additive noise in the EEG data if necessary. This noise is caused by external surroundings and the noise from the measurement equipment. An average frequency spectrum of non-seizure EEG data is computed over a period of time to provide an estimate of the noise spectrum. As the EEG data is recorded, it is transformed to the frequency domain. The average noise frequency spectrum is then subtracted from the EEG frequency spectrum. The resultant frequency spectrum and phase information from the original noisy signal are then combined and the result is transformed back to the time domain, resulting in a de-noised EEG signal. This allows the method to be implemented in different clinical or non-clinical environments where adaptive compensation for additive stationary noise may be required.

In step 206, the EEG data is segmented into epochs of a set duration, typically 256 samples in duration with each epoch having a 50% overlap with neighbouring epochs. It will be understood that 256 samples corresponds to the downsampled EEG signal that has in essence been sampled at 32 Hz. An epoch is 2048 samples in duration, in relation to the 256 Hz EEG signal.

Steps 200 to 206 have been carried out on the EEG data on the combination of channels. In step 207 and onwards, analysis is carried out on each channel separately.

In step 207, the EEG data is standardized by eliminating the effect of the montage that was used in gathering the EEG data. Independent Componenet Analysis (ICA) is used to provide this montage elimination. Furthermore, each source is then examined using complexity measures to eliminate sources containing noise.

Next a Non-negative Matrix Factorisation (NMF) algorithm is applied to each channel as a form of artifact removal. The spectrum of the signal is decomposed into the extracted bases as defined in the training phase and the weights are obtained. The spectrum which is reconstructed using the bases of artifacts and corresponding weights is then removed from the initial signal, in a similar fashion to spectral subtraction, to provide an artifact free representation.

Next, in step 208, features are then extracted from each epoch of each channel. Such features include features from the frequency domain, time domain, time-frequency domain, information theory, nonlinear-dynamics system theory, modelling approaches and speech recognition techniques. Preferably, the list of eighty-six features listed in relation to the training phase are extracted for each epoch. The extracted features are then combined in a feature vector for use with the classifier.

In step 210, the EEG data is classified as to whether it relates to a seizure or nor-seizure. The feature data that has been extracted from the EEG data using the feature extraction techniques is fed to the multi-patient trained generic Support Vector Machine (SVM) classifier. The feature data comprises a feature vector for each epoch. Each feature vector comprises values for each feature that has been extracted and calculated for that epoch. The SVM then computes an SVM channel seizure output for each feature vector. The SVM channel seizure output will have a magnitude and sign, the sign indicates whether the epoch is classified as a seizure or non-seizure epoch, while the magnitude indicates the confidence of the classification. The greater the magnitude of the output, the more likely the epoch has been correctly classified. The SVM channel seizure outputs are converted to the probability-like values with the formula of Platt [Probabilistic outputs for SVM and comparison to Regularized likelihood methods, J. Platt, 1999] whose parameters of sigmoid function are obtained from the training data. In this way the SVM channel seizure outputs are normalized between 0 and 1 and the performance of the system slightly increases in comparison to the direct usage of SVM distances.

In the operational phase, the classifier from the training phase is applied separately to each channel. Given that the SVM is a binary classification system, the SVM channel seizure output of the classification stage is a measure of confidence in the presence or absence of a seizure in each channel for each epoch. The higher the absolute value of the SVM channel seizure output, the higher the distance of the testing point from the separating hyper-plane within the SVM and thus the higher the confidence that its sign shows the correct label. Using the confidences it is possible to control the conversion of the SVM channel seizure output to a binary channel seizure decision by choosing different levels of confidence. Alternatively, if the SVM channel seizure outputs have been converted to probabilities, the choice would be in relation to class priors. In this way, a clinician could choose the sensitivity of the detection method on a patient by patient basis. The SVM channel seizure output of the SVM classifier is computed for each feature vector, converted to probability, compared to 0.5 and a binary channel seizure decision is generated based on that comparison. However, if the clinician wanted to identify seizures that with a higher confidence, the probability value could be compared to 0.6 or higher as desired, and the binary decision generated based on that comparison. Similarly, the comparison value may be lowered to include less confident seizure detections. The binary channel seizure decision indicates which of the two possible decisions, seizure or non-seizure, has been indicated by the classifier. I In step 212, the SVM binary channel seizure decisions for all channels are fused together to generate an SVM epoch seizure decision, which indicates the presence or absence of a seizure in that epoch. The fusion operates such that, if there is a seizure at least in one channel the whole epoch is marked as a seizure, otherwise non-seizure. Therefore the fusion operation is in essence a logical OR operator. If, optionally, the SVM channel seizure outputs have not been converted to SVM binary channel seizure decisions, the SVM channel seizure outputs may be fused by the OR operator to form an SVM epoch seizure output.

Once the classification of step 210 has been completed, and the channel fusion in step 212, a number of post-processing operations are carried out in step 214 on the data. Firstly, a linear moving average filter (MAF) is applied to the time sequence of confidences, decisions or probabilities. In each channel as an optimal filter to reduce random noise while retaining a sharp step response thus helping to avoid too frequently alternating labels. The moving average filter uses a rectangular window function having a filter order of 15 epochs Secondly, the collar technique, known from speech activity detection tasks is applied. Every seizure decision is extended from either side by some amount of time to compensate for possible difficulties in detecting pre-seizure and post-seizure parts. The choice of the collar length is to be defined based on the data analysis, e.g. collar of 40 s can be applied. If the window parameters of the epoch, that is the epoch duration and overlap percentage, change, so too will the moving average filter order and collar to achieve the similar performance. However, for some choices of window length and overlap, performance degradation is unavoidable regardless of filtering and collar.

In step 216, the method of the invention provides an SVM epoch seizure decision indicating whether it believes the current epoch of EEG data indicates the occurrence of a seizure or not.

Figure 3:
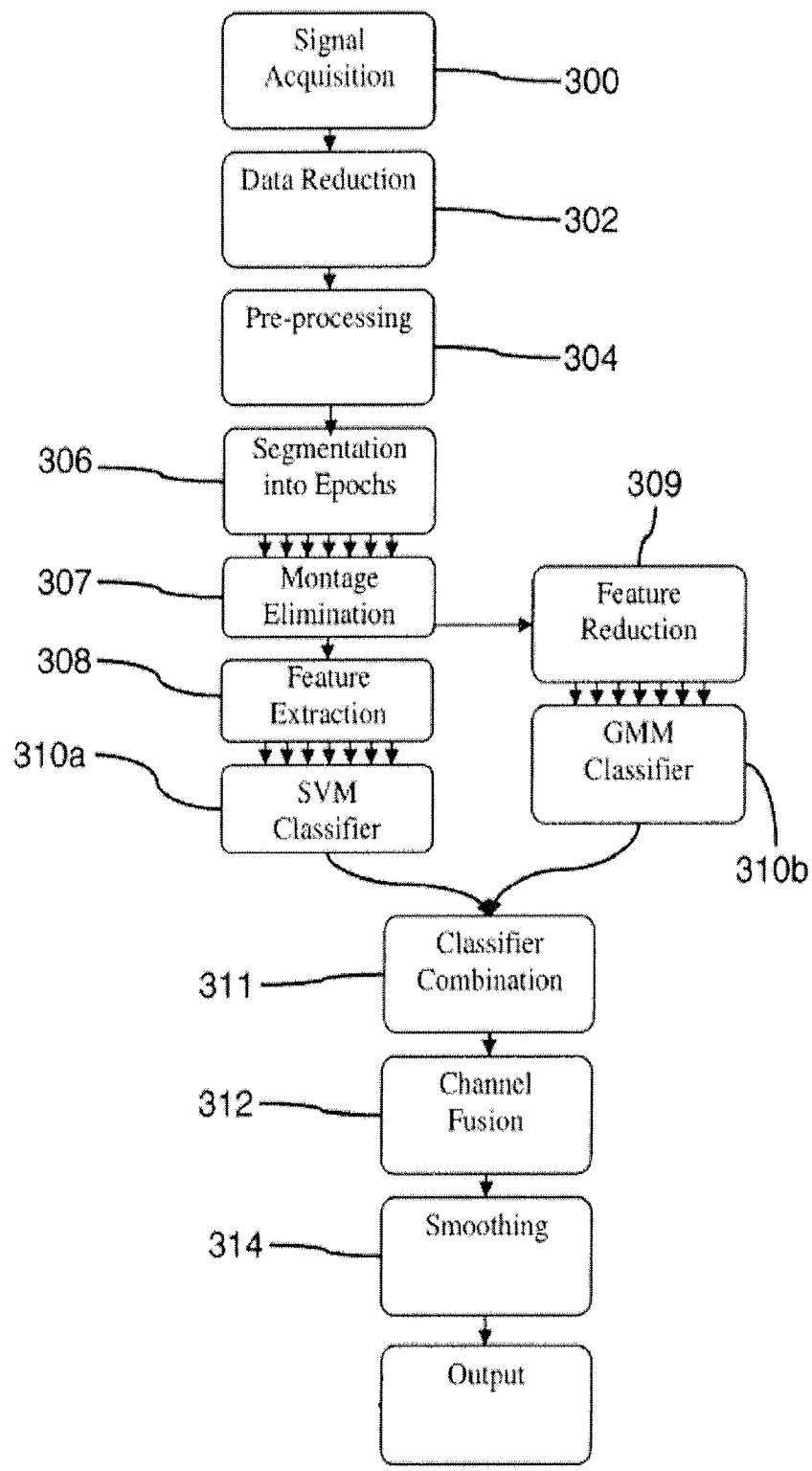
FIG. 3 is a flow chart of an alternative method according to the invention.

A further embodiment of the invention, as illustrated in FIG. 3, includes the use of a Gaussian Mixture Model (GMM) based statistical classification system. Both the SVM and GMM classifier systems takes as input a datapoint and assigns it to a class label. The combination of the classifiers is based on the analysis of the diversion of results obtained by the SVM and GMM classifiers. The analysis of the diversity showed that the two classification systems tend to have errors in different situations. The diversity of the SVM and GMM classifiers guarantees that the correct combination of the results of the SVM classifier and the GMM classifier will improve seizure identification results.

A Gaussian Mixture Model (GMM) represents the probability density function of a random variable as a weighted sum of several Gaussian distributions. The parameters of the GMM are computed using the Expectation Maximisation algorithm. In the training phase, it is necessary to fit several Gaussians (e.g. 8) onto the data of each class—seizure and non-seizure—assuming that they can be modelled by mixtures of several Gaussians. The GMM is trained in the same way as the SVM, using 5-fold cross validation to estimate parameters. The same training data set as used to train the SVM classifier is also used to train the GMM classifier. The parameters themselves are estimated at each fold using expectation maximization (EM: A. P. Dempster, N. M. Laird, and D. B. Rubin, "Maximum likelihood from incomplete data via the EM algorithm," Journal of the Royal Statistical Society. Series B (Methodological), vol. 39, no. 1, pp. 1-38, 1977) In order to reduce the complexity of the GMM training stage and increase the accuracy, the features are transformed and the feature dimensionality is reduced using the pre-processing steps of Principal Component Analysis (PCA) and Linear Discriminant Analysis (LDA). The PCA provides a decorrelated feature vector, the dimensionality of which is reduced by the LDA such that in combination the number of features is reduced while still retaining as much useful information as possible in the feature vector. The feature dimensionality reduction methods produce a transformation matrix which is then used to provide the necessary feature dimensionality reduction in the operational phase. The pre-processed data are then fed to train the GMM model per class.

In use, steps 300 to 308 of the method illustrated in FIG. 3 are the same as those described in relation to FIG. 2. In step 309, the feature vector is transformed into a reduced feature vector using PCA and LDA as described above.

In step 310a the feature vector is processed by the SVM classifier at the same time as the reduced feature vector is processed by the GMM classifier in step 310b, generating an SVM channel seizure output and a GMM channel seizure output for each epoch respectively. In step 311 the channel seizure outputs of the SVM and GMM classifiers are combined to form a combined channel seizure output or each epoch. The combination of the channel seizure outputs from multiple classifiers implemented using a weighted arithmetic mean. The weights used for combination have been calculated using cross-validation tests. Preferable weights are 0.7 for SVM channel seizure outputs and 0.3 for GMM channel seizure outputs. The channel seizure outputs for each classifier are first converted into probabilities and then the probabilities of seizure in both classifiers are combined. The probability of seizure in the first channel given by GMM and SVM are weighted and summed to give the final probability of the seizure in that first channel and so on.

Channel fusion is implemented either at probability level, taking the mean of the probabilities of seizure across all channels and comparing to a threshold to obtain a binary result, or at a decision level, by comparing the probability of seizure in each channel to a threshold to obtain a binary result for each channel and then using an OR operator to obtain a single binary decision.

Then, the same post-processing as described in relation to FIG. 2 is applied to the combined probabilities in each channel. In step 312, the combined channel seizure outputs from each channel for a certain epoch are fused using an OR operator as before, forming a combined epoch seizure output. Then in step 314, the sequence of combined epoch seizure outputs are smoothed using the moving average and collar technique. Optionally, each combined epoch seizure output may be converted to a combined epoch seizure decision before smoothing.

In additional embodiments of the invention, further improvement in the results of the analysis can be provided using dynamic classifiers.

In an alternative embodiment of the invention, the SVM classifier is replaced with a dynamic SVM classifier, that is a multi-patient trained generic Support Vector Machine (SVM) classifier that uses sequential kernels. This is a dynamic classifier that takes account of the temporal information in the EEG signal, and learns to recognize the temporal evolution of a seizure. A drawback of SVMs when dealing with audio data is their restriction to working with fixed-length vectors. Both in the kernel evaluation and in the simple input space dot product, the units being processed are vectors of constant size. However, when working with EEG signals, although each signal epoch is converted into a feature vector of a given size, the whole event is represented by a sequence of feature vectors, which shows variable length. In order to apply an SVM to this kind of data, a suitable kernel function capable of dealing with sequential data is used instead of the Gaussian kernel. The dynamic time warping kernel is used to implement the dynamic SVM classifier that may be used with the method of the invention. The dynamic SVM classifier is trained and implemented in the same manner as the SVM classifier.

The steps of the method using the dynamic SVM are similar to those described in relation to FIGS. 1, 2, and 3. The dynamic SVM classifier is trained on the same training data and in the same manner as the SVM classifier. The EEG signal is preprocessed and features are extracted in the same manner as earlier patents. The feature vector for each epoch is fed to the dynamic SVM classifier and a dynamic SVM channel seizure output is generated. The dynamic SVM channel seizure outputs may be fused across the channels to generate a dynamic SVM epoch seizure output is the dynamic SVM classifier is used on its own. Alternatively, the dynamic SVM classifier may be combined with other classifiers such as the standard SVM classifier, or the GMM classifier. In such a case the dynamic SVM channel seizure outputs are combined with the channel seizure outputs from the other classifiers for each epoch, thereby generating a dynamic SVM combined seizure output. The dynamic SVM combined seizure outputs are then fused across all channels for the epoch in question using the OR operator as before, generating a dynamic SVM combined epoch seizure output. The dynamic SVM combined seizure outputs and dynamic SVM combined epoch seizure outputs may be converted to probability values as described above.

The use of the weighted arithmetic mean can be used to combine the dynamic classifier results with the static SVM and GMM results.

In a further embodiment of the invention, the method operates to identify seizure, non-seizure and artefact data in the EEG signal. This multi-class decision process provides more accurate classification and in the preferred embodiment classifies artefacts into separate categories, providing invaluable artefact information to clinicians. The method of the invention comprises a number of features that are useful for the elimination of noise and other artefacts from the data signals. Spectral subtraction is used to reduce the amount of additive noise, while obvious, large-scale, short-term artifacts are removed at the pre-processing stage of the method using Non-Negative Matrix Factorisation. Additionally, the step of montage elimination using Independent Component Analysis (ICA) also further reduces noise from the signal. However, those artefacts that are more similar in characteristic to seizure data need to be removed in a more advanced manner. As SVM is a binary classifier; it can classify only between two classes. If there are more than two classes considered, such as seizure, non-seizure and artefact, a number of SVM classifiers must be implemented. To provide an SVM classifier capable of distinguishing between seizure, non-seizure and artefact, a number of binary classification routines are employed. These comprise three classification branches. The first branch classifies seizure vs. non-seizure. This corresponds to the main SVM classifier of the invention and provides SVM channel seizures outputs. The second classifies seizure vs. artifact. This provides SVM artefact channel outputs. The third classifies non-seizure vs. artefact, providing further SVM artefact channel outputs. The final result is determined using majority voting. In order to implement this artifact identification method, the training data set must be annotated so as to identify the artifacts. Otherwise, the training steps of the method are identical to those outlined in relation to FIG. 1.

The method of the invention further optionally includes the additional post-processing step of utilising the Viterbi algorithm which is particularly suited for use with an SVM classifier. The Viterbi is a dynamic programming algorithm for finding the most likely sequence of hidden states—called the Viterbi path—that results in a sequence of observed events, especially in the context of Markov information sources, and more generally, hidden Markov models. The forward algorithm is a closely related algorithm for computing the probability of a sequence of observed events. These algorithms belong to the realm of information theory. Viterbi can be applied either after each classifier before they are fused, or on the result of the fused classifiers.

In either case the implementation of the algorithm itself is known from HMM/Viterbi: Lawrence R. Rabiner, "A tutorial on Hidden Markov Models and selected applications in speech recognition". Proceedings of the IEEE 77 (2): 257-286, February 1989

Figure 4:
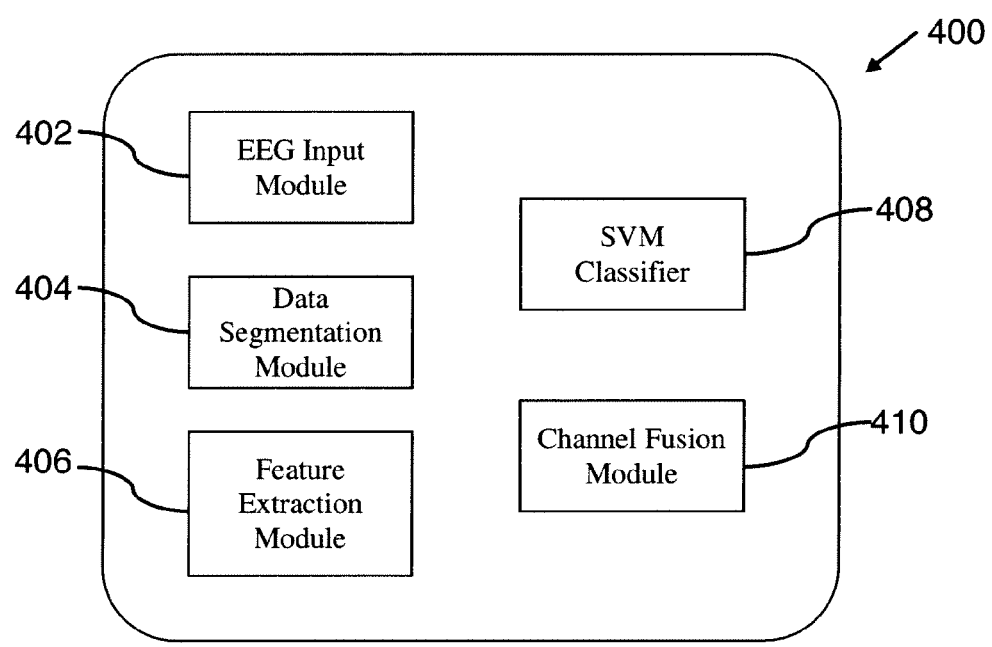
FIG. 4 is a block diagram of an exemplary system in which the method of the invention may operate.

Referring now to FIG. 4, there is shown a block diagram of an exemplary apparatus in which the method of FIG. 1 may operate. The apparatus, generally indicated by the reference numeral 400, comprises an EEG Input Module 402 comprising means for receiving an EEG signal comprising at least one channel of EEG data and a Data Segmentation Module 404 comprising means for segmenting the data of each channel into a sequential epochs such that each epoch has an overlap with its neighbouring epochs. The apparatus 400 further comprises a Feature Extraction Module comprising means for extracting features from each epoch of the constituent channels and means for generating a feature vector from the extracted features. An SVM classifier 408 is also comprised within the apparatus 400, the SVM classifier 408 comprising a multi-patient trained generic SVM classifier. The SVM classifier 408 is trained over on EEG data representing all seizure types, over all channels and over all patients. The SVM classifier 408 receives the feature vector from the Feature Extraction Module 406, processes the feature vector for each epoch and generates an SVM channel seizure output indicative of the seizure activity within that epoch of that channel. Finally the apparatus comprises a Channel Fusion Module 410 comprising means for fusing the SVM channel seizure outputs for all channels thereby generating an SVM epoch seizure output, indicative of the seizure activity present in that epoch across all channels.

It will be understood by the person skilled in the art that the apparatus described in relation to FIG. 4 may be easily adapted to implement any of the other embodiments of the invention described herein. For example, further classifier modules may be included such as a GMM classifier and dynamic SVM classifier. If further classifier modules are included, it will be understood that a classifier combination module will also be included, comprising means to combine the classifier seizure outputs to form combined classifier seizure outputs. It will be further understood that the apparatus 400 may be implemented in software, hardware, firmware or any other suitable manner and the invention is not limited to any particular manner of implementation.

Throughout the specification, the term real-time has been used to refer to the operation of a method wherein the start of a seizure is identified in the EEG signal before the seizure is completed. In operation, this will be understood to refer to a method wherein an epoch of the EEG signal is analysed before the next epoch has been recorded.

In the specification the terms 'comprise', 'comprises', 'comprised' and 'comprising' or any variation thereof and the terms 'include', 'includes', 'included' or 'including' or any variation thereof are considered to be totally interchangeable and they should all be afforded the widest possible interpretation.

The invention is not limited to the embodiment herein described, but may be varied in both construction and detail within the terms of the claims.

The invention claimed is:

1. A method for the real-time identification of seizures in an Electroencephalogram (EEG) signal, the steps of the method comprising:
   (a) receiving an EEG signal comprising a plurality of channels of EEG data;
   (b) for each of the plurality of channels of EEG data, segmenting the data into sequential epochs, each of the sequential epochs having an overlap with its neighboring sequential epochs;
      and for an initial epoch of each of the plurality of channels performing the following steps comprising:
   (c) extracting forty five or more features from each of the plurality of channels of EEG data;
   (d) generating a feature vector from the extracted features;
   (e) passing the feature vector for each of the plurality of channels of EEG data separately through a multi-patient trained generic Support Vector Machine (SVM) classifier and generating SVM channel seizure outputs for each feature vector, in which the multi-patient trained generic support vector machine classifier is trained on EEG data representing all seizure types, over all channels and over all patient types;
   (f) fusing the SVM channel seizure outputs for all channels thereby generating an SVM epoch seizure output, the SVM epoch seizure output indicative of a seizure activity present in that epoch across all channels; and
   (g) repeating steps (c) to (f) for each of the subsequent sequential epochs thereby generating a sequence of SVM channel seizure outputs and SVM epoch seizure outputs; and
   (h) providing an SVM epoch decision to a user, the SVM epoch decision being indicative of whether the EEG data indicates the occurrence of a seizure or not.

2. The method as claimed in claim 1 further comprising the additional steps of:
   generating a reduced feature vector; passing the reduced feature vector through a multi-patient trained Gaussian Mixture Model (GMM) classifier; and
   generating a GMM channel seizure output.

3. The method as claimed in claim 2 further comprising the additional step of combining the SVM channel seizure output and GMM channel seizure output for each of the sequential epochs thereby generating a combined channel seizure output for each of the sequential epochs for each of the plurality of channels.

4. The method as claimed in claim 3 further comprising the additional step of fusing the combined channel seizure outputs for each of the sequential epochs across all channels thereby generating a combined epoch seizure output for each of the sequential epochs.

5. The method as claimed in claim 1 further comprising the additional step of converting each of the sequence of SVM channel seizure outputs into a binary channel seizure decision.

6. The method as claimed in claim 1 further comprising the additional step of converting each of the sequence of SVM channel seizure outputs to a normalised probabilistic value between 0 and 1.

7. The method as claimed in claim 1 in which the step of fusing the SVM channel seizure outputs comprises using a logical OR operator.

8. The method as claimed in claim 1 further comprising the additional step of applying a moving average filter to the sequence of SVM epoch seizure outputs.

9. The method as claimed in claim 1 further comprising the additional step of applying a collar technique to the sequence of SVM epoch seizure outputs.

10. The method as claimed in claim 1 in which the step of extracting features from the plurality of channels of EEG data comprises extracting features using speech recognition analysis techniques.

11. The method as claimed in claim 1 in which the step of extracting features from the plurality of channels of EEG data comprises extracting features using time domain analysis techniques, frequency domain analysis techniques and information theory analysis techniques.

12. The method as claimed in claim 1 in which the method comprises the additional step of passing the feature vector through a Support Vector Machine (SVM) with sequential kernels and generating a dynamic SVM channel seizure output.

13. The method as claimed in claim 1 further comprising passing the feature vector through the multi-patient trained generic SVM classifier and generating an SVM channel artefact output.

14. A computer program product stored on a non-transitory carrier having computer program instructions for causing a computing device to perform the method of claim 1.

15. An apparatus for the real-time identification of seizures in an Electroencephalogram (EEG) signal, the apparatus comprising:
means for receiving an EEG signal comprising a plurality of channels of EEG data;
means for segmenting the data of each channel into a plurality of sequential epochs, each of the plurality of sequential epochs having an overlap with its neighboring plurality of sequential epochs;
means for extracting forty five or more features from each of the plurality of channels of EEG data for each of the plurality of sequential epochs;
means for generating a feature vector from the extracted features for each of the plurality of sequential epochs for each of the channels of EEG data;
a multi-patient trained generic Support Vector Machine (SVM) classifier adapted to process the feature vector so as to generate SVM channel seizure outputs for each of the plurality of sequential epochs, wherein the multi-patient trained generic SVM classifier is trained on EEG data representing all seizure types, over all channels and over all patient types; and
means for fusing the SVM channel seizure outputs for each of the channels thereby generating an SVM epoch seizure output indicative of a seizure activity present in that epoch across all channels; and
means for providing an SVM epoch decision to a user, the SVM epoch decision being indicative of whether the EEG data indicates the occurrence of a seizure or not.

16. The apparatus as claimed in claim 15 further comprising:
means for generating a reduced feature vector;
means for passing the reduced feature vector through a multi-patient trained Gaussian Mixture Model (GMM) classifier and generating a GMM channel seizure output for each of the plurality of sequential epochs;
means for combining the SVM channel seizure output and GMM channel seizure output for each of the plurality of sequential epochs thereby generating a combined channel seizure output; and
means for fusing the combined channel seizure outputs for each of the plurality of sequential epochs across all of the plurality of channels of EEG data thereby generating a combined epoch seizure output for each of the plurality of sequential epochs.

17. The apparatus as claimed in claim 15 further comprising means to convert each of the SVM channel seizure outputs into a binary channel seizure decision.

18. The apparatus as claimed in claim 15 further comprising means to apply a moving average filter to a sequence of SVM epoch seizure outputs.

19. The apparatus as claimed in claim 15 further comprising means to apply a collar technique to a sequence of SVM epoch seizure outputs.

* * * * *